United States Patent
Natvig

Patent Number: 6,055,672
Date of Patent: May 2, 2000

[54] EAR HELD EARMUFF

[76] Inventor: Tom Natvig, Sätunavägen 13, S-740 30 Björklinge, Sweden

[21] Appl. No.: 09/347,804

[22] Filed: Jul. 2, 1999

Related U.S. Application Data

[63] Continuation of application No. PCT/SE98/00001, Jan. 2, 1998.

[30] Foreign Application Priority Data

Jan. 3, 1997 [SE] Sweden .................. 9700011

[51] Int. Cl.[7] ...................................... A42B 1/06
[52] U.S. Cl. .................................... 2/209; 2/208
[58] Field of Search ................ 2/209, 208; 128/864, 128/866

[56] References Cited

U.S. PATENT DOCUMENTS 2,378,398  6/1945  Fiedler .
2,582,907  1/1952  Kaufmann .
3,112,493  12/1963  Greenberg .
4,713,843  12/1987  Duncan .
4,791,684  12/1988  Schwartz .
4,872,219  10/1989  Duncan .
5,339,467   8/1994  Brinkley .

*Primary Examiner*—Bibhu Mohanty
*Attorney, Agent, or Firm*—Frommer, Lawrence & Haug LLP

[57] ABSTRACT

Protective ear covering and method of producing the same, comprising enclosing a flexible, cupshaped insert which may be turned against a biasing force to bulge from a position wherein an ear is insertable through an opening of the insert to a position wherein the insert is attached around the ear, the method including that the insert is attached to the wrong side of the stitched clothing and then turned through its own opening together with the clothing for turning the clothing right.

5 Claims, 2 Drawing Sheets

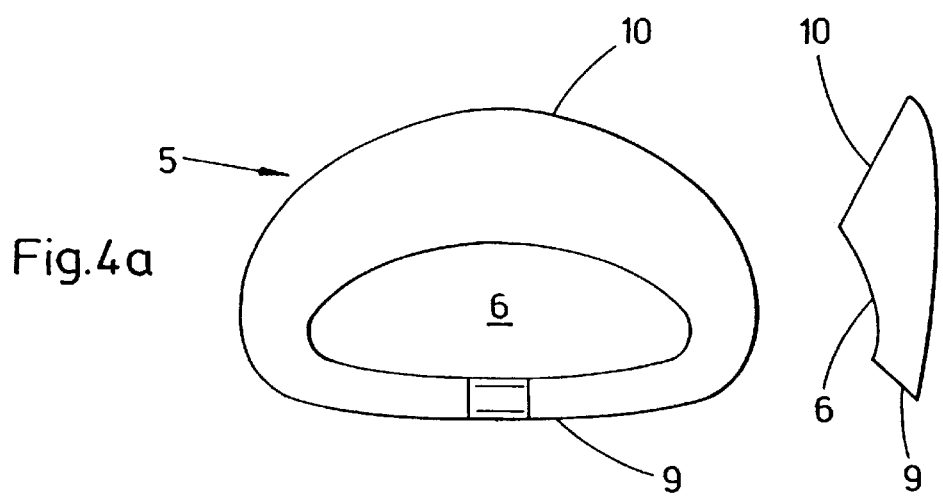
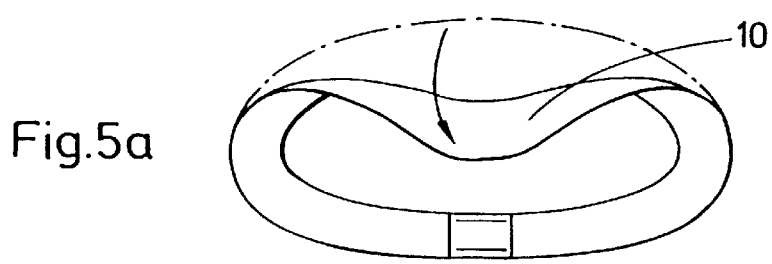
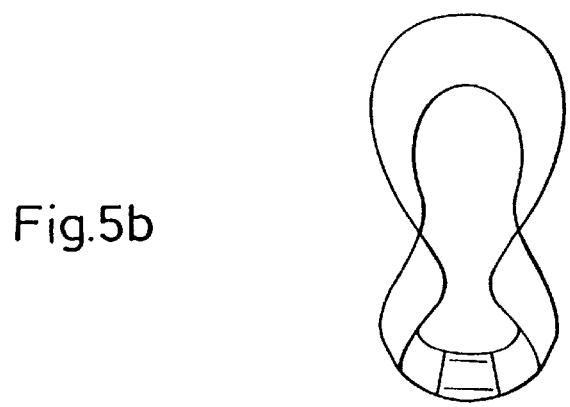
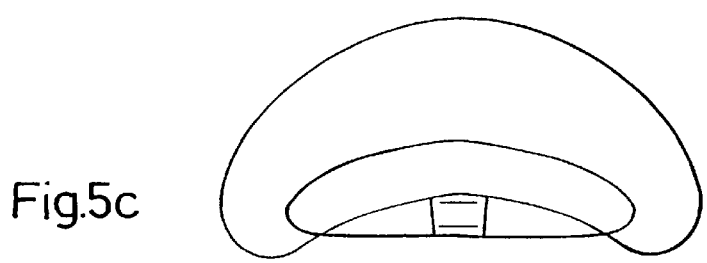

EAR HELD EARMUFF

This is a continuation of copending International Application PCT/SE98/00001 having an international filing date of Jan. 2, 1998.

The present invention refers to a protective ear covering of the type which has a flexible insert, covered by an insulating clothing and with an oval opening for insertion of an ear. The ear covering is flexible to be bulged to either side against the bias of the flexible insert. More specifically, the invention refers to a simplified and more effective method for attaching the clothing to the insert, and an ear covering produced by the inventive method.

From patent documents, several ear coverings are known with the general characteristics of the inventive ear covering. A common feature of known ear coverings having a flexible and shiftable insert, however, is that the insulating clothing is at least partly stitched to the periphery of the insert and/or stitched to the rim of the opening through which the ear is introduced when wearing the covering. Known ear coverings are e.g. disclosed in U.S. Pat. Nos. 5,339,467, 4,872,219 and 3,112,493. The method of producing the disclosed ear coverings is characterized by a stitching step, including the flexible insert which is generally made from a plastic material. Naturally, for a uniform quality of production, stitching machines of high demands are required, as well as needles and precision of work.

In contrast to this known technology, the invention provides an ear covering and a method of producing the same, the object of which is to simplify and to increase effectiveness of production.

This object is met in the invention by providing a method wherein the covering is completely stitched and finished, before it is attached to the flexible insert.

The inventive method is characterized by the features of the attached independent claim, and embodiments of the invention are listed in the subclaims.

The invention is more fully described below with reference made to the attached drawings, of which FIG. 1 shows the stitching of the clothing, effectuated on two layers of cloth, fabric or equivalents;

FIGS. 4a and 4b shows the insert in an elevational view from above and from one of its sides, resp., and FIGS. 5a, 5b and 5c shows the turning of the insert inside out in three successive steps.

Figure 1:
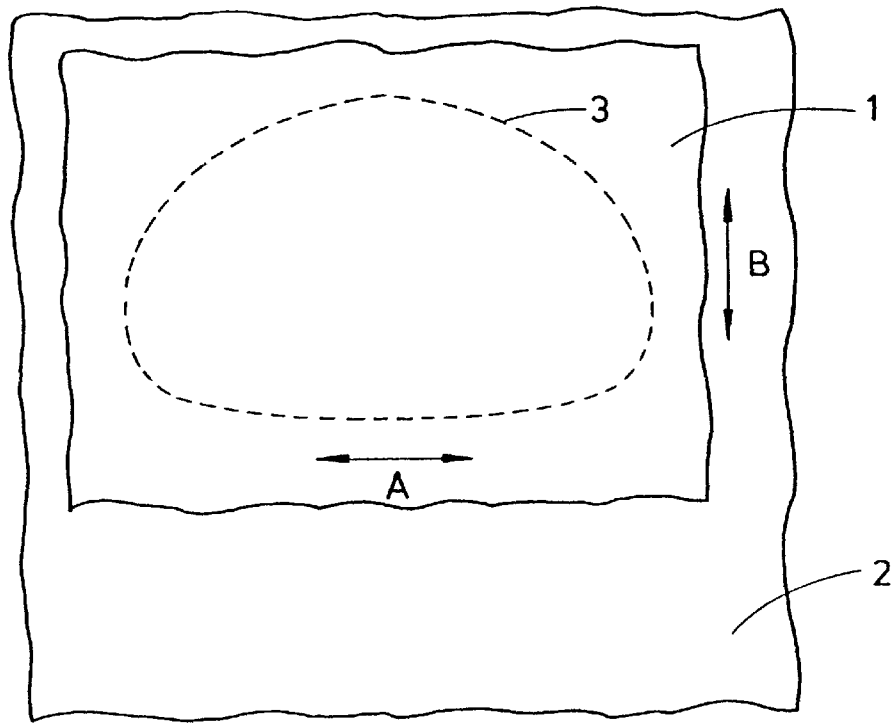
Figure 2:
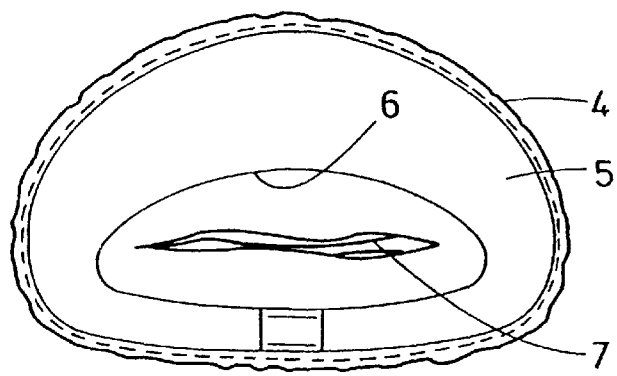
FIG. 2 shows the stitched clothing, cut out and placed in an insert.
Figure 3:
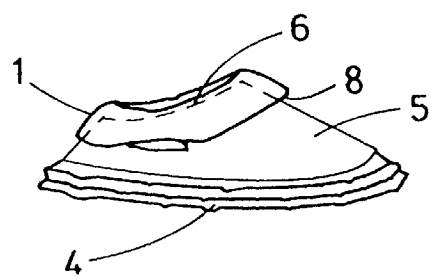
FIG. 3 shows the stitched and cut out clothing, one layer of which is adhered to the rim of the insert opening.

The inventive method of production mainly comprises three steps:

a) stitching of the clothing (FIG. 1);
b) attaching the clothing to the insert (FIG. 2 and FIG. 3), and
c) turning the insert and clothing outside in (FIG. 4 and FIG. 5).

The clothing may advantageously be chosen from cold or heat insulating cloth or synthetic fibre material. The material may in at least one direction exhibit a substantial elasticity, but may also be elastic in the other directions with no significant direction of inherent elasticity.

When stitching the clothing, two layers 1,2 of the material are placed face to face in such way, that the superimposed layers provide good elasticity in two, substantially transversely intercrossing directions A,B. The layers of material are then stitched together along a periphery line 3 of the ear covering, the main elasticity of one of the layers aligned with the longitudinal direction of the elliptical ear covering. The stitching may be effected in a programmable stitching machine, or in a manual manner assisted by a prototype model. After stitching, the ear cover clothing 4 is finished in a cutting or punching step.

The clothing is attached to a flexible insert 5 of plastic material. The insert is formed in adaptation to a human ear, having an oval and substantially elliptic opening 6 for insertion of the ear. The insert is cup-shaped, having one concave and one convex side, resp., but is turnable against a biasing force to bulge to one or the other side. The material of the insert may advantageously be plastic of even thickness, e.g. softened PVC, and may be moulded into shape or punched from a plane sheet, cut in one longitudinal side and closed by joining the slit side with the cut edges overlapping each other, thereby producing the cup-shaped insert.

The clothing 4, right sides facing inwards, is placed on the concave side (inside) of the cup-shaped insert, the cloth layer having its main elasticity in the longitudinal direction of the ear covering placed in contact with the insert. A straight slit 7 is cut in said cloth layer, centrally to the insert opening and extended within the periphery of the opening. An adhering compound, e.g. a dissolving adhesive, is applied around the rim of the insert opening, and the cut edges 8 of the cloth layer are turned through the opening and pressed against the convex side (outside) of the insert for adhering around the rim of the insert opening.

Finally, the ear covering is turned right by turning the insert and its adhered clothing through the insert opening, from the concave side to the convex side of the insert. By turning the insert through its own central opening, the insert will be positioned inside the stitched double layer clothing, which is simultaneously turned outside in to have its wrong sides and sewing margins facing inwards.

The turning is made possible by chosing for the insert a suitable material as said above, and by forming the insert substantially as is disclosed by FIG. 4. As can be appreciated from the drawing, the insert comprises a relatively straight and narrow front section 9, at the ends of the ear covering successively changing into a relatively wide and significantly bow-shaped back section 10. Said back section 10 provides the main part of the inherent bias of the finished ear covering and which operates to hold the cover to the users ear. The narrow front section operates mainly as a drawing strap which maintains the biasing shape for the back section. The size of the opening, together with the smaller width of the front section support the turning operation which advantageously is initiated by pressing the widest part of the back section downwards through the centre of the opening, see FIG. 5a. Then, the turning motion is continued longitudinally towards the ends of the ear cover, and past the same as in FIG. 5b, so that finally the front section is turned outside in through the insert opening, FIG. 5c. For reasons of clearity, the turning maneuvre is shown without the clothing. However, the clothing will not complicate the turning operation, when a material having proper elasticity is chosen for the ear cover clothing. Fleece® is an example of a suitable synthetic material with cold insulating properties, but also other woven or knitted materials of synthetic or nature fibres may be suitable, if providing a certain elasticity.

An ear covering produced by the inventive method is characterized by the lack of visible seems or stitchings and comprises no peripheral margins, as is the case of known ear covers. The ear covering of the invention includes a smoothly rounded periphery, thereby making it comfortable to wear.

To increase the cold protecting ability, a third material layer may be included in the ear cover clothing, the ear covering thereby comprising double layers on the outside. Said third layer may be adhered to the wrong side of layer 2, representing the outside of the ear covering. The third layer may be somewhat smaller to cover the area inside the stitching margin, thereby facilitating the stitching and turning of the ear covering. The third layer, if desired, is advantageously adhered after the stitching together of the first two layers of cloth.

What is claimed is:

1. Method of producing a protective ear covering, wherein a plastic insert is formed to be cup-shaped and flexible to be bulged to one side or the other against an inherent bias, and the insert is enclosed in a clothing, comprising the steps of:

a) stitching the clothing;
   b) attaching the clothing to the insert, and
   c) turning outside in the insert with the clothing attached thereto.

2. Method of claim 1, further comprising the steps of;

a) stitching together at least two layers of cloth placed face to face and with respective main directions of elasticity thereof transversely intercrossing to produce the clothing;
   b) cutting a longitudinal slit in one layer of cloth having its direction of elasticity aligned with a longitudinal direction of the ear covering;
   c) placing the stitched together at least two layers on the inside of the cup-shaped insert so that the cut longitudinal slit is positioned in center of an opening formed by the insert;
   d) applying adhesive on the outside of the insert, and turning the edges of the one layer of cloth defining said slit through the opening for adhering the stitched at least two layers to the outside of the insert, and
   e) turning the insert and stitched at least two layers outside in through the opening, whereby the insert is placed between the stitched at least two layers.

3. Ear covering, comprising:

an enclosed flexible plastic insert having the shape of a cup including an inherent bias against which the insert is flexible to bulge to one side or the other, said flexible plastic insert having a first side to be positioned adjacent a user's head and a second side to be positioned away from a user's head, and defining an oval opening for insertion of an ear; and
   a stitched clothing cover, wherein the stitched clothing cover is only attached to the insert in an area thereof which surrounds the oval opening on said second side of said flexible plastic insert, and wherein the clothing cover passes through the insert opening and encloses the insert inside the clothing cover thereby covering said oval opening from said second side of said insert, but maintaining said oval opening from said first side of said insert.

4. Ear covering of claim 3, wherein the clothing includes at least two layers of material, the main directions of elasticity of which are transversely intercrossing.

5. Ear cover of claim 3, wherein one of the layers of material is doubled.

* * * * *